United States Patent
Op Den Buijs (10) Patent No.: US 11,043,100 B2
(45) Date of Patent: Jun. 22, 2021

(54) METHOD FOR DETECTING FALL OF A USER

(71) Applicant: KONINKLIJKE PHILIPS N.V., Eindhoven (NL)

(72) Inventor: Jorn Op Den Buijs, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/808,531

(22) Filed: Mar. 4, 2020

(65) Prior Publication Data

US 2020/0294381 A1 Sep. 17, 2020

(30) Foreign Application Priority Data

Mar. 12, 2019 (EP) .................................... 19162147

(51) Int. Cl.
| | |
|---|---|
| G08B 21/04 | (2006.01) |
| A61B 5/11 | (2006.01) |
| G01P 15/18 | (2013.01) |
| G08B 29/26 | (2006.01) |
| G08B 31/00 | (2006.01) |

(52) U.S. Cl.
CPC ........ *G08B 21/0446* (2013.01); *A61B 5/1117* (2013.01); *G01P 15/18* (2013.01); *G08B 21/043* (2013.01); *G08B 29/26* (2013.01); *G08B 31/00* (2013.01); *A61B 2560/0257* (2013.01)

(58) Field of Classification Search
None
See application file for complete search history.

(56) References Cited

U.S. PATENT DOCUMENTS

| | | | |
|---|---|---|---|
| 2011/0246114 A1 | 10/2011 | Jin | |
| 2013/0307696 A1* | 11/2013 | Booij | G01S 5/021 340/686.6 |
| 2016/0220153 A1* | 8/2016 | Annegarn | G08B 21/0446 |
| 2018/0174420 A1 | 6/2018 | Clark et al. | |
| 2019/0086116 A1* | 3/2019 | Buchanan | F24F 7/08 |

(Continued)

FOREIGN PATENT DOCUMENTS

| | | |
|---|---|---|
| DE | 102017203672 A1 | 9/2018 |
| EP | 3296841 A1 | 3/2018 |

(Continued)

OTHER PUBLICATIONS

Carrie et al., "Uncertainties in Building Pressurisation Tests Due to Steady Wind," Science Direct, Energy and Buildings 116, pp. 656-658. (Year: 2016).*

(Continued)

*Primary Examiner* — Nabil H Syed
*Assistant Examiner* — Cal J Eustaquio (57) ABSTRACT

A computer implemented method for detecting a fall of a user within an internal space of a building, the method comprising receiving a first air-pressure sensor signal indicative of change in air-pressure measured at a device worn by the user; receiving a measurement indicative of change in air-pressure within the internal space of the building; and determining the fall of the user based on the change in air-pressure measured at the device and the measurement indicative of change in air-pressure within the internal space of the building.

15 Claims, 6 Drawing Sheets

(56) References Cited

U.S. PATENT DOCUMENTS

2020/0159960 A1* 5/2020 Jakobsson ........... G06F 21/6245

FOREIGN PATENT DOCUMENTS

WO     2004/114245 A1    12/2004
WO     2010055450 A1     5/2010

OTHER PUBLICATIONS

International Search Report and Written Opinion dated May 8, 2020 for International Application No. PCT/EP2020/055986 Filed Mar. 6, 2020.
Gallagher FW, Fredrickson SE, Gallagher Iii FW. Meteorological pressure-sensor inaccuracies. 2000;381(10). [doi: 10.1119/1.1324540].
Liu H, Darkow GL. Wind Effect on Measured Atmospheric Pressure. J Atmos Ocean Technol Feb. 1, 1989;6(1):5-12. [doi: 10.1175/1520-0426(1989)006<0005:WEOMAP>2.0.CO;2].

\* cited by examiner

METHOD FOR DETECTING FALL OF A USER

FIELD OF THE INVENTION

The present invention relates to the field of monitoring a user, in particular, in the field of detecting a fall of the user.

BACKGROUND OF THE INVENTION

Personal emergency response systems (PERS) can improve the quality of life for elderly living on their own while providing ease of mind to their loved ones. These systems typically make use of a body worn device such as wristband or neck-worn pendant. During an emergency, the subscriber presses an emergency push button on the device, which establishes a two-way call with the service provider's call center.

The body-worn fall detection device such as a wrist-based device or pendant worn around a user's neck usually incorporates a pressure sensor(s) because pressure sensors are effective in realizing high accuracy in detecting height changes. Such body-worn fall detection devices are mostly used by seniors in the home and are affected by internal building pressure. However, internal building pressure is known to be altered by elevated (external) wind speeds, such as during a thunderstorm. Therefore, pressure readings by a pressure sensor in the body-worn device are affected by external wind speed.

Pressure sensor-based fall detectors are based on the fact that pressure changes with changes with elevation. A simple version of the vertical fluid pressure variation is:

$$\frac{dP_h}{dh} = -\rho g$$

Here $P_h$ is pressure, h is height, g is acceleration of gravity (9.81 kg m/s2) and $\rho$ is density of air (1.2 kg/m3 at sea level). A height drop dh=−1.0 m then results in a pressure increase $dP_h$=12 Pa.

Figure 1A:
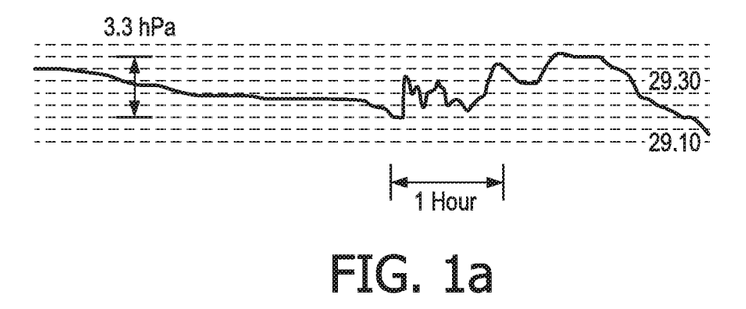
FIG. 1a shows microbarograph pressure trace (in inches of mercury) recorded at NSSL during passage of a strong thunderstorm in Norman, Okla., in March 1990.
Figure 1B:
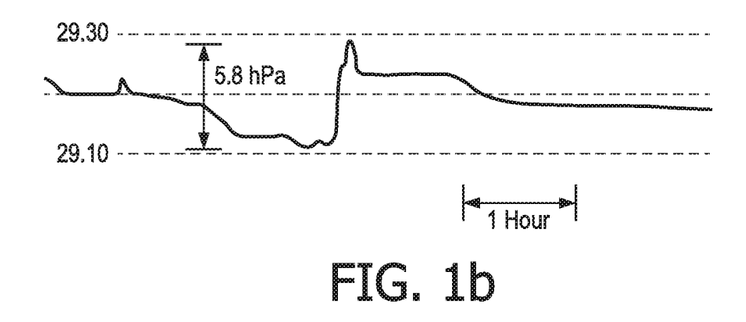
FIG. 1b shows microbarograph pressure trace (in inches of mercury) recorded at NSSL during passage of a strong thunderstorm in Norman, Okla., in May 1989.
Figure 1C:
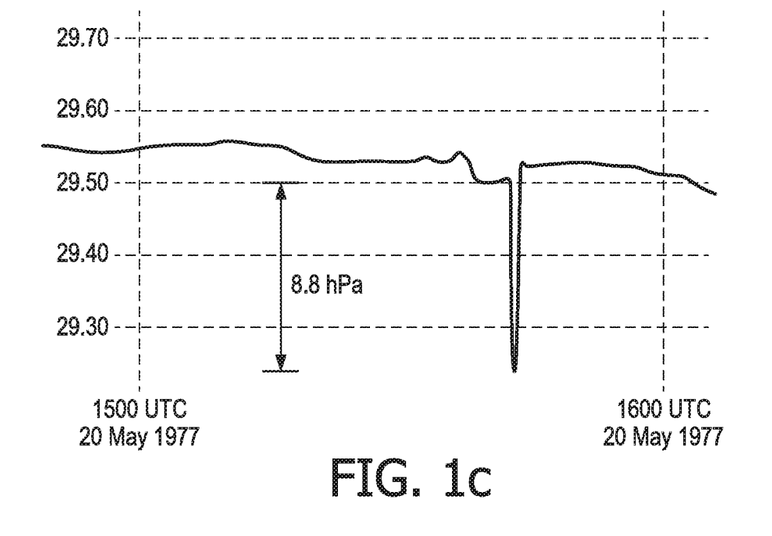
FIG. 1c shows microbarograph pressure trace (in inches of mercury) recorded at NSSL during passage of a weak tornado at Chickasha, Okla., on May 20, 1977.

Wind affects barometric pressure readings by superimposing a dynamic pressure on the true atmospheric pressure (cf. Gallagher F W, Fredrickson S E, Gallagher Iii F W. Meteorological pressure-sensor inaccuracies). This dynamic pressure varies with the square of the wind velocity. Even in case doors and windows are closed during wind, the effect of wind on indoor pressure readings is not negligible. Examples of indoor pressure changes during passages of thunderstorms and tornadoes are given in FIGS. 1a, 1b and 1c. FIG. 1a shows microbarograph pressure trace (in inches of mercury) recorded at NSSL during passage of a strong thunderstorm in Norman, Okla., in March 1990. Largest pressure changes were on the order of 3 hPa. Time increases toward right of figure. FIG. 1b shows microbarograph pressure trace (in inches of mercury) recorded at NSSL during passage of a strong thunderstorm in Norman, Okla., in May 1989. Largest pressure changes were on the order of 3 hPa. Time increases toward right of figure. FIG. 1c shows microbarograph pressure trace (in inches of mercury) recorded at NSSL during passage of a weak tornado at Chickasha, Okla., on May 20, 1977. Largest pressure changes were on the order of 9 hPa. Time increases toward right of figure.

Assume that an external gust of wind produces an additional component over its static value, also known as the dynamic pressure $P_d$, where:

$$P_d = \tfrac{1}{2} \rho v^2$$

Here is the wind speed in m/s. Further assume that the indoor pressure variance as a result of an (external) gust of wind can be approximated as to be proportional to the variation of this dynamic pressure component $P_d$:

$$\frac{dP_i}{dP_a} = \beta$$

Where $\beta$ is a coefficient that is dependent on the characteristics (volume, ventilation) of the home. Research has indicated that $\beta = -0.5$ (approximately) for a typical two-story building with uniform wall openings and some roof vents (cf. Liu H, Darkow G L. Wind Effect on Measured Atmospheric Pressure. J Atmos Ocean Technol 1989 Feb. 1;6(1): 5-12). Assuming that after a gust of wind, wind speed decreases from 6.3 m/s to 0 m/s, and as a result, $dP_d$=−24 Pa, then the internal building pressure increases by 12 Pa. This pressure increase is identical to a pressure increase as a result of a 1.0 m drop in height.

Thus, a decrease in external wind speed may be regarded by a pressure sensor-based fall detector as a height drop that resembles a fall. Furthermore, time till steady-state of internal pressure due to external wind dynamics is of the order of 0.5-10 s depending on building characteristics and windows/doors being open/closed. This is of the same order of magnitude as the time of a fall (a free fall from 1.0 m height takes 0.45 s). Therefore, it will be difficult to distinguish a pressure variation due to wind speed variation from a pressure variation due to a fall. This increases false alarm rates (i.e. inaccurate fall detection) and thus the user dissatisfaction.

WO2010055450A1 patent application also filed by the applicant already discloses a solution for detecting the fall in such bad weather conditions. The solution therein proposes to ignore the fall detected based on air-pressure measured at the device during bad weather and use accelerometer/motion data only to detect the fall of the user.

SUMMARY OF THE INVENTION

It is an object of the present invention to provide an improved system for detecting a fall of a user, such as an elderly.

In a first aspect of the present invention a computer implemented method for detecting a fall of a user within an internal space of a building, the method comprising receiving a first air-pressure sensor signal indicative of change in air-pressure measured at a device worn by the user; receiving a measurement indicative of change in air-pressure within the internal space of the building; and determining the fall of the user based on the change in air-pressure measured at the device and the measurement indicative of the change in air-pressure within the internal space of the building.

The invention as claimed provides advantage that determination of the fall is based on realization of changed pressure in the building due to bad weather, such as thunderstorms. This increases accuracy of the detection and thus improves attending to the fall of the user and other critical situations.

The term building used herein means the house/apartment where the user is located. For instance, a two-story house. For a skilled person it should be clear that an air pressure measured due to wind will be very different at the $25^{th}$ floor of a building vs at the $1^{st}$ floor.

In a further embodiment, the measurement indicative of change in the air-pressure within the internal space of the building is received from an air-pressure sensor placed at a fixed height within the internal space of the building. The air-pressure sensor is preferably located in a vicinity, such as the same floor, where the use is located. For instance, the air-pressure sensor can be affixed to one of the walls in the room where the elderly is residing. Another example could be a base unit that is in communication with the device worn by the user itself and that the base unit incorporates the pressure sensor. Yet another example could be a thermostat incorporating the pressure sensor. The advantage of the pressure sensor being fixed at a fixed height is that it can be used to correct for internal building pressure changes measured by the body-worn air-pressure sensor. Subsequently, the air pressure measured by the body-worn sensor can then distinguish pressure changes due to changes in height from changes in internal building pressure.

In a further embodiment, the measurement indicative of change in the air-pressure within the internal space of the building is calculated based on a wind speed, preferably real time wind speed, at the exterior/outside of the building. The wind speed can be provided by a wind speed sensor installed at the outside or rooftop of the building. Alternatively, the wind speed can be provided by a local weather station. Advantageously, this helps in correcting the air pressure measured at the device, thus giving true measure of the pressure indicative of fall.

In a further embodiment, the measurement indicative of change in the air-pressure within the internal space of the building is derived based on a statistical measure of the air-pressure measured in a plurality of buildings in a neighborhood. In a preferred embodiment, an average of pressure measured in the device worn by the body and/or at a base unit in communication with the device in plurality of homes/buildings is performed. Given that there are less chances many users will fall at the same time the average of the measured pressure is indicative of the internal building pressure. A change in pressure measured by the body-worn pressure sensor of the individual can then be corrected by changes in this average of the measure pressure. If there is still a change in the corrected air-pressure, this will be indicative of a height change and potentially a fall of the user. Advantageously, this way avoids the need of additional pressure sensor/wind sensor/or interface with external weather station that provides wind speed information.

In a further embodiment, determining the fall of the user further includes determining an air-pressure value based on the change in the air-pressure measured at the device and the measurement indicative of change in the air-pressure within the internal space of the building; comparing the air-pressure value with a pre-determined air-pressure threshold; and determining the fall based on the comparison. The air pressure value thus calculated based on the change in the air-pressure measured at the device and the measurement indicative of change in the air-pressure within the internal space of the building is indicative of change of height of the user and/or change in pressure due to change in height, which can be indicative of fall.

In a second aspect of the present invention, an apparatus configured for detecting a fall of a user within an internal space of a building, the apparatus comprising an air-pressure interface configured for receiving a first air-pressure sensor signal indicative of change in air-pressure measured at a device worn by the user; a building air pressure interface for receiving a measurement indicative of change in air-pressure within the internal space of the building; and a processing unit configured for determining the fall of the user based on the change in air-pressure measured at the device and the measurement indicative of change in air-pressure within the internal space of the building.

In a further embodiment, the building air pressure interface receives the measurement indicative of change in the air-pressure within the internal space of the building from an air-pressure sensor placed at a fixed height within the internal space of the building.

In a further embodiment, the building air pressure interface receives the measurement indicative of the change in air-pressure within the internal space of the building from the processing unit, wherein the processing unit calculates the measurement indicative of the change in air-pressure within the internal space of the building based on a wind speed at the exterior/outside of the building.

In a further embodiment, the wind speed is received from at least one of a wind sensor module placed at the exterior/outside of the building and a weather station.

In a further embodiment, the wind speed is a real-time wind speed.

In a further embodiment, the building air pressure interface receives the measurement indicative of the change in the air-pressure within the internal space of the building from the processing unit, wherein the processing unit calculates the measurement indicative of the change in air-pressure within the internal space of the building based on a statistical measure of the air-pressure measured in a plurality of buildings in a neighborhood of the building.

In a further embodiment, the processing unit is configured to determine the fall by determining an air-pressure value based on the change in air-pressure measured at the device and the measurement indicative of the change in air-pressure within the internal space of the building; comparing the air-pressure value with a pre-determined air-pressure threshold; and determining the fall based on the comparison. The air pressure value thus calculated based on the change in the air-pressure measured at the device and the measurement indicative of change in the air-pressure within the internal space of the building is indicative of change of height of the user and/or change in pressure due to change in height, which can be indicative of fall.

In a further embodiment, the apparatus as described above is part of a device configured to be worn by a user. The device further includes an air pressure sensor configured to measure an air-pressure at the device worn by the user.

In a further embodiment, the device as described above is part of a system configured for detecting a fall of a user. The system further includes a wind sensor module and/or a weather station configured to provide a wind speed at the exterior/outside of a building of the user.

In yet further aspects of the present invention, there is provided a corresponding computer program which comprises program code means for causing a computer to perform the steps of the methods disclosed herein when said computer program is carried out on a computer as well as a non-transitory computer-readable recording medium that stores therein a computer program product, which, when executed by a processor, causes the method disclosed herein to be performed.

In various embodiments, the change in pressure either at the device worn by the user or the measurement indicative of change in air pressure within the internal space of the building is the change over time, i.e. at least at two time instances. The measurements can be taken in real time and then difference can be computed to measure any change that is indicative of a fall.

It shall be understood that the apparatus, the device and the system and computer program product claims will have similar advantages as the computer implemented method claims.

Preferred embodiments of the invention are defined in the dependent claims. It shall be understood that the apparatus, the device and the system and computer program product can have similar and/or identical preferred embodiments/advantage(s) as the claimed computer implemented method, in particular as defined in the dependent claims and as disclosed herein.

BRIEF DESCRIPTION OF THE DRAWINGS

These and other aspects of the invention will be apparent from and elucidated with reference to the embodiment(s) described hereinafter. In the following drawings.

DETAILED DESCRIPTION OF THE DRAWINGS

Figure 2:
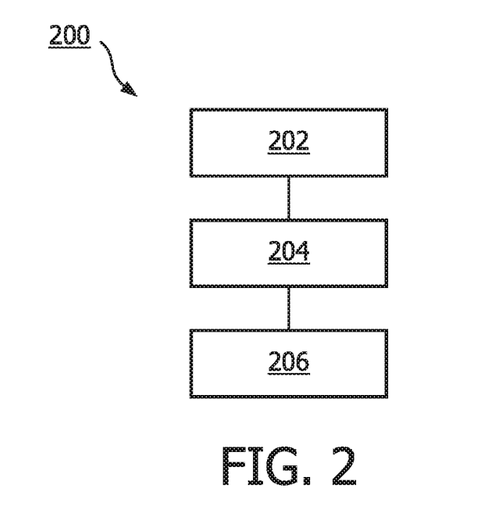
FIG. 2 shows a flowchart depicting the computer implemented method of detecting a fall of a user within an internal space of a building according to an embodiment.

FIG. 2 shows a flowchart 200 depicting the computer implemented method of detecting a fall of a user within an internal space of a building according to an embodiment.

At step 202, a first air-pressure sensor signal indicative of change in air-pressure ($dP_m$) measured at a device worn by the user, also referred to as a wearable device, is received. The air-pressure measured at the device is indicative of the height at which the device is worn by the user.

In an embodiment, the first air-pressure signal is received from an air-pressure sensor incorporated in the device that the user is wearing. Examples of air-pressure sensors are piezoelectric-based sensors, piezoresistive strain-gauge pressure sensors, capacitive sensors, optical sensors. Various examples of the device may include but are not limited to a neck-worn device, a wrist-worn device, a chest-worn device, and the like.

At step 204, a measurement of change in air-pressure ($dP_i$) within the internal space, such as a room, of the building is received. This measurement is indicative of the air-pressure in the room where the user is located. There are various alternatives by which the measurement indicative of an air-pressure within the internal space can be received. For instance, wind speed sensor module, such as anemometer, local weather station, or a pressure sensor installed at a fixed height, such as in a thermostat, within the internal space of the building, or average internal pressure measured in houses within the same neighborhood of the user.

At step 206, the fall of the user is determined based on the change in air-pressure measured at the device and the measurement indicative of change in air-pressure within the internal space of the building. In an embodiment, the fall is determined based on the change of pressure ($dP_h$) corresponding to the change of height, detected at the device worn by the device. It may be appreciated that change in a pressure value is indicative of change of height. The determination of change of pressure due to change of height is further explained below in conjunction with FIG. 3.

Figure 3:
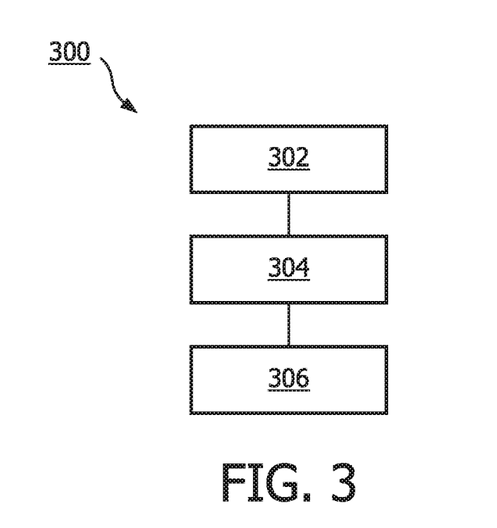
FIG. 3 shows a flowchart depicting the computer implemented method of determining the fall of the user based on the air-pressure measured at a device worn by the user and a measurement of the air-pressure within the internal space of the building according to an embodiment.

FIG. 3 shows a flowchart depicting the computer implemented method of calculating determining the fall of the user based on the air-pressure measured at the device worn by the user and a measurement indicative of the air-pressure within the internal space of the building according to an embodiment.

As described above, the fall is determined based on the change in a pressure value corresponding to the change of height, detected at the device worn by the device. Thus, at step 302, the air-pressure value based on the air-pressure measured at the device and the measurement indicative of the air-pressure within the internal space of the building is determined. The (change in) pressure value indicative of height change and/or change in height can be calculated in several ways. These alternatives are explained below.

Alternative 1—Wind speed sensor module: The wind speed (v) can be received via an anemometer preferably located on the roof of the home of the user. Alternatively, the wind speed could be derived from real time measurements from a local weather station. Thereafter, the changes in the square of the wind speed can be calculated and synchronized with the changes in the first air-pressure signal. This synchronization can be done using time stamp and/or by finding the maximum correlation of the measured pressure changes with the wind speed.

It may be noted that the air-pressure change measured by the air-pressure sensor at the device worn by the user, $dP_m$, is the sum of the internal building pressure change ($dP_i$) (due to wind speed) and any pressure change ($dP_h$) due to height changes:

$$dP_m = dP_i + dP_h = \tfrac{1}{2}\beta\rho d(v^2) - \rho g dh$$

Wherein:

g is acceleration of gravity (9.81 kg m/s$^2$);

$\beta$ is a coefficient that is dependent on the characteristics (volume, ventilation) of the home. Research has indicated that $\beta = -0.5$ (approximately) for a typical two-story building with uniform wall openings and some roof vents (cf. Liu H, Darkow G L. Wind Effect on Measured Atmospheric Pressure. J Atmos Ocean Technol 1989 Feb. 1;6(1):5-12);

d($v^2$)–the change of quadratic wind speed, wherein d($v^2$)=$v^2$(t)–$v^2$(t–td); and $$dP_m = P_m(t) - P_m(t-td);$$

ρ=density of air (1.2 kg/m³ at sea level);

$dP_i$=½βρd($v^2$); and
$dP_h$=–ρg dh
t=a time instant
td=a time instant ata delay Given that $dP_m$ and $dP_i$ are the measurements that come/derived/received from the measurements at the device worn by the device and from the wind sensor module respectively, $dP_h$ is accordingly calculated.

Figure 3A:
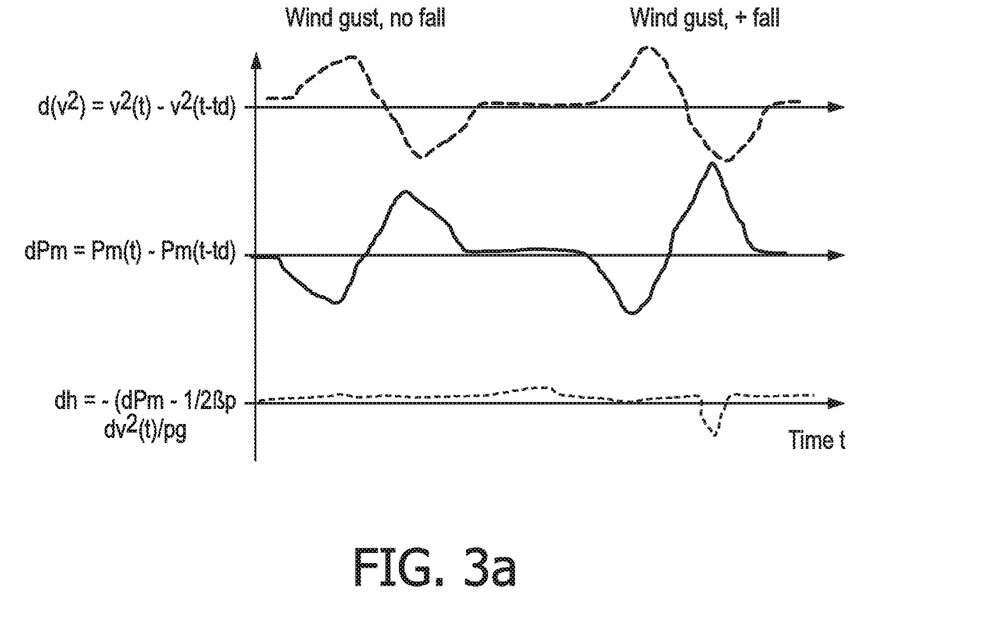
FIG. 3a shows estimation of height changes (dh) after correction for internal building pressure changes ($dP_i$).

Further, the change in height, i.e. dh, can be further calculated as dh=$dP_h$/ρg. Furthermore, the effect of the wind on the measured pressure at the wearable device is also depicted in FIG. 3a.

Figure 3B:
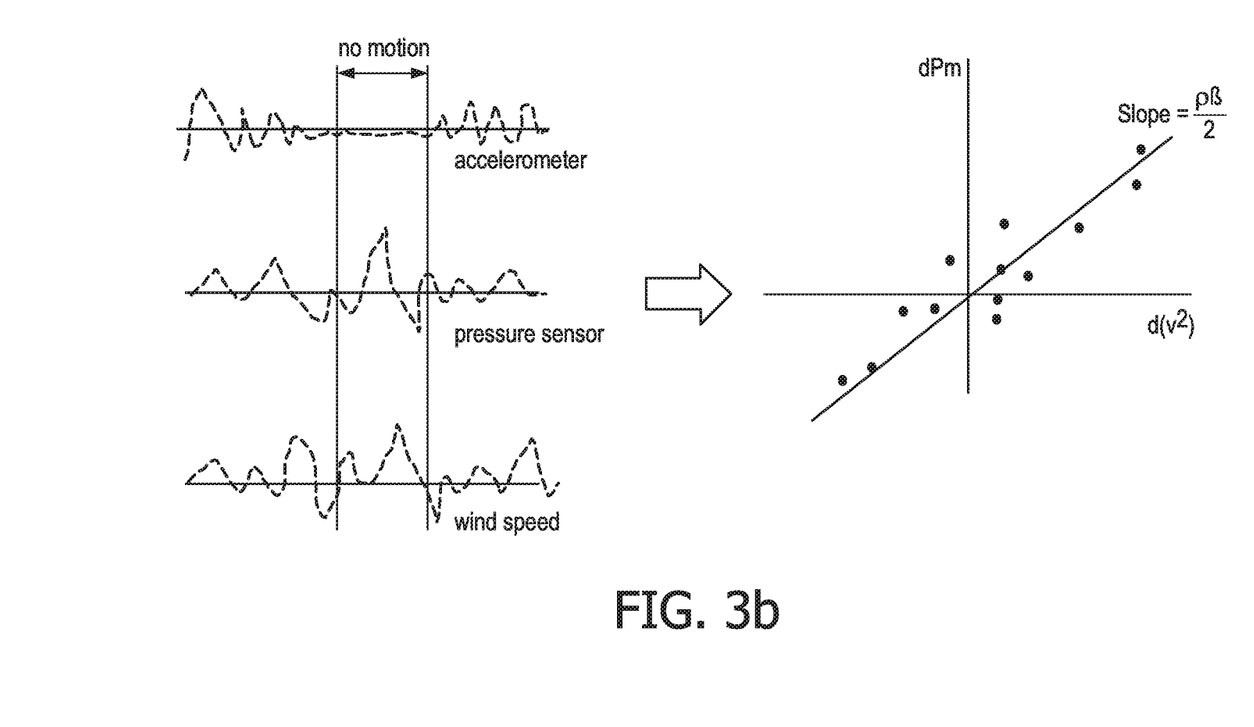
FIG. 3b shows calculation/determination of $\beta$ using regression in another embodiment.

As explained above, β is a coefficient that have a predetermined value. Alternatively, it can be also estimated based on the sensor data. This coefficient can be computed from a linear regression of changes in the measured pressure signal dPm signal—measured via the air-pressure sensor in the device that the user has worn for detecting fall—vs. the change of quadratic wind speed d($v^2$)—measure by a wind speed sensor module at the roof top of the home. The regression line will be forced to go through the origin (0,0). Furthermore, to avoid influence of pressure changes due to elevation changes in this regression, the signal from an accelerometer sensor (also included in the device worn by the user) is used to determine when the air-pressure sensor is not in motion and the regression is only performed for measurements when the pressure sensor was not moving. This is also depicted in FIG. 3b.

Alternative 2—A pressure sensor installed at a fixed height, such as in a thermostat, within the internal space of the building: As explained earlier, the change in air-pressure measured by the air-pressure sensor at the device worn by the user, $dP_m$, is the sum of the internal building pressure change ($dP_i$) (due to wind speed) and any pressure change ($dP_h$) due to height changes:

$$dP_m = dP_i + dP_h$$

The effect of the wind on the internal building pressure is determined by measuring the changes in the internal building pressure via another pressure sensor in the home, preferably one that does not change in height and preferably, located in vicinity/proximity of the user. For instance, the sensor should not be in 15$^{th}$ floor of the building when the user is in 1$^{st}$ floor. However, a typical house of 2-3 stories is fine as the pressure change is more or less the same. The preferred scenario would be that the additional pressure sensor is located at the same floor as where the user is located. This additional sensor for instance, can be located in a PERS communicator (base unit that communicated with the wearable device), smart thermostat, or a dedicated pressure sensor just fixed to a wall of the house.

The height changes are then corrected by taking the difference of the two changes in pressure signals:

$$dh = -\frac{dP_m - dP_i}{\rho g}$$

In an embodiment, changes in the internal building pressure and changes in the pressure signal from the additional pressure sensor or the additional pressure sensor in a PERS communicator/thermostat are synchronized. This synchronization can be done using time stamp and/or by finding the maximum correlation of the two measured pressure changes with each other.

Alternative 3—Average internal pressure signal of peer users: As also explained in previous two alternatives, the change in air-pressure measured by the air-pressure sensor at the device worn by the user, $dP_m$, is the sum of the change in internal building pressure ($dP_i$) (due to wind speed) and any changes in pressure ($dP_h$) due to height changes:

$$dP_m = dP_i + dP_h$$

The internal building pressure signal ($P_i$) is derived by synchronizing and averaging multiple measurements of change in pressure of 'n' users in similar homes in the same area.

$$dP_i(t) = dP_m1 + dP_m2 + dP_m3 + dP_m4 + \ldots + dP_mn/n$$

It is practical to assume that in a sample set of 'n' users that the average of pressure measured at the device worn by the user will be indicative of the weather condition itself since the pressure measured at the device is a combination of pressure due to weather and pressure due to height of the user. Given that there are less chances many users will fall at the same time the average of the measured pressure is indicative of the internal building pressure. A change in pressure measured by the body-worn pressure sensor of the individual can then be corrected by changes in this average of the measure pressure. If there is still a change in the corrected air-pressure, this will be indicative of a height change and potentially a fall of the user. Advantageously, this way avoids the need of additional pressure sensor/wind sensor/or interface with external weather station that provides wind speed information.

The change in internal building pressure for the user is then estimated as the average of the measured signals in users 1, 2, . . . , n. Thus, a pressure difference between the pressure measured at the device worn by the user and the measured average internal building will be indicative of a fall of the user.

The height changes are then corrected by taking the difference of the two change in pressure signals:

$$dh = -\frac{dP_m \text{user} - dP_i(t)}{\rho g}$$

Thus, to conclude at the step 302, any of the alternatives discussed above can be used to determine the change in height of the user/or change in pressure indicative of change in height of the user to further determine the fall of the user.

Thereafter, at step 304, the calculated pressure value ($dP_h$) and/or change in height (dh) is compared with a pre-determined air-pressure threshold or pre-determined height corresponding to the pre-determined air-pressure threshold. It is anticipated that changes in elevation during a fall are of the order of 0.5-1.5 m within a time of about 0.45 s. This corresponds to pressure increases of 6-18 Pa. Therefore, thresholds for fall detection based on pressure change are in the range 6-18 Pa, with a preferred value of 12 Pa. A height drop dh=–1.0 m then results in a pressure increase dP=12 Pa. Furthermore, dP may be further adjusted based on local pressure and temperature.

Thus, if the change in the pressure ($dP_h$) exceeds 12 Pa or change in height exceeds 1 m, then a fall is determined at step 306.

Optionally, when it is estimated that change in building pressure (dP$_i$) itself exceeds 12 Pa [not (dP$_h$)], then:

the detection threshold may be increased with the estimated component dPi to decrease falls alarms at the cost of a lower detection rate; or switch of fall detection altogether until the estimated component dP$_i$ is below the threshold of ~12 Pa; or switch to accelerometer-based fall detection; or Correct the estimated height changes with the estimated internal pressure change component dP$_i$.

Figure 4:
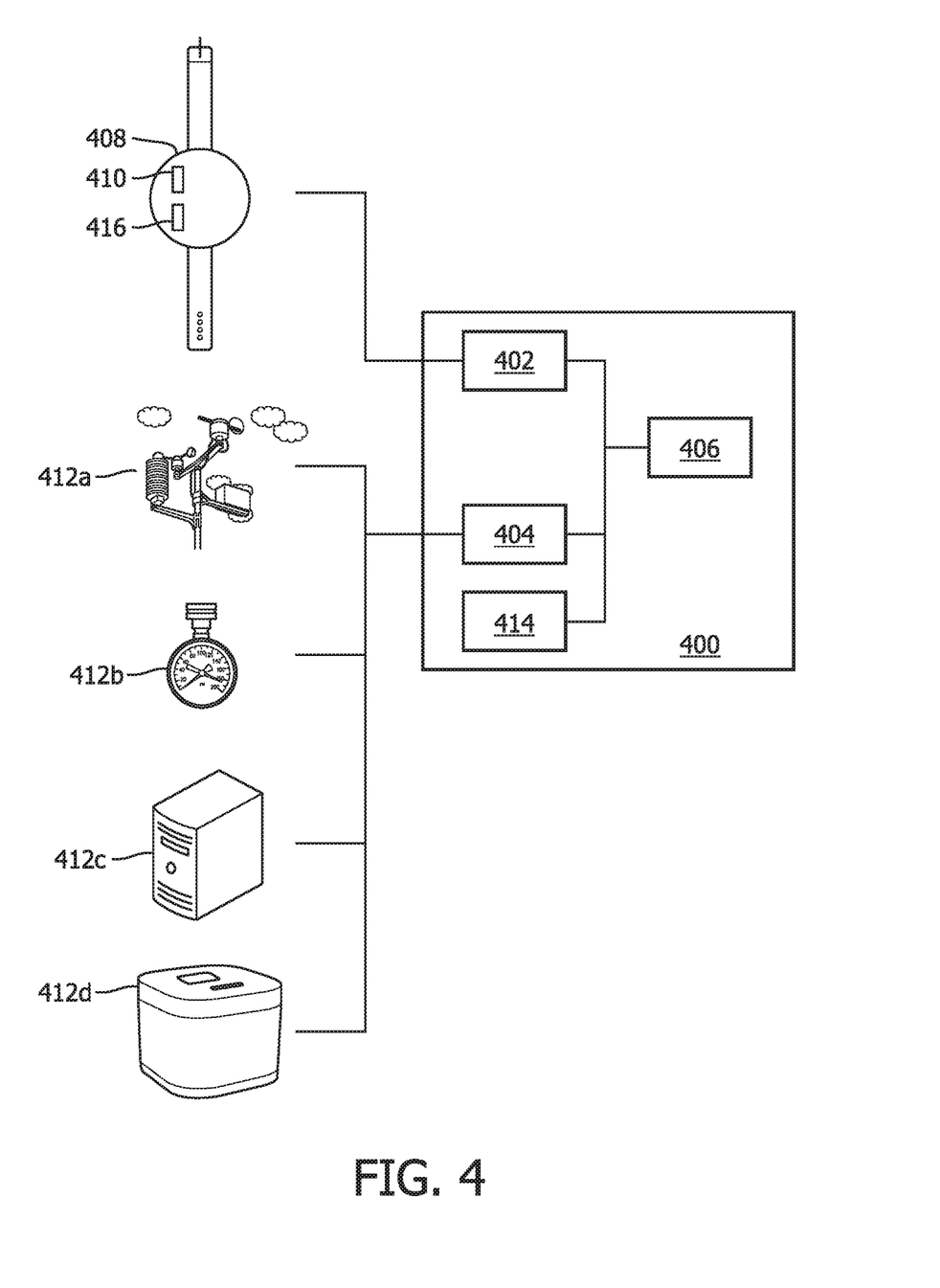
FIG. 4 shows a device for detecting a fall of a user within an internal space of a building according to an embodiment.

FIG. 4 shows a device 400 for detecting a fall of a user within an internal space of a building according to an embodiment.

The device 400 includes an air-pressure interface 402, a building air pressure interface 404 and a processing unit 406.

The air-pressure interface 402 is configured for receiving a first air-pressure signal indicative of change in air-pressure measured at a device 408 worn by the user, also may be referred to as a wearable device 408. The air-pressure signal is provided by an air-pressure sensor 410 included in the device 408. The air-pressure interface 402 may be implemented as hardware and/or software. Although the device 408 is shown as a wrist worn device, it may be appreciated that the device 408 may be as well a neck worn device, a chest worn device, etc.

The building air pressure interface 404 for receiving a measurement indicative of change in air-pressure within the internal space of the building. The measurement indicative of the air-pressure within the internal space of the building is either received directly from an air-pressure sensor 412b placed at a fixed height on a wall of the internal space where the user is located or integrated in a communicator/base unit 412d that interacts with the device 408. This has been further explained earlier in conjunction with Alternative 2.

Alternatively, the processing unit 406 derives the measurement indicative of change in the air-pressure within the internal space of the building based on the wind speed outside the building and provides the measurement to the building air-pressure interface 404. The wind speed can be provided by a weather station 412c or a wind speed sensor 412a, such as anemometer, place at the exterior of the building/house, preferably at the rooftop of the house. The processing unit 406 then computes the measurement indicative of change in the air-pressure within the internal space of the building based on the received wind speed as explained earlier in conjunction with Alternative 1.

Alternatively, the processing unit 406 derives the measurement indicative of change in the air-pressure within the internal space of the building based on the average of the pressure measured at the devices, similar to device 408, worn by the users in a particular neighborhood and accordingly provides the measurement to the building air pressure interface 404. The computation is further explained earlier in the Alternative 3. The building air pressure interface 404 may be implemented as hardware and/or software.

The processing unit 406 is further configured for determining the fall of the user based on the air-pressure measured at the device and the measurement of change in the air-pressure within the internal space of the building. The processing unit 406 determines the fall of the user by executing the method steps as described earlier in conjunction with FIG. 3.

Alternatively, /optionally, the device 400 includes an accelerometer interface 414. The accelerometer interface 414 receives accelerometer data from an accelerometer 416 optionally included in the wearable device 408. In a scenario when the processing unit 406 determines that change in building pressure (dP$_i$) itself exceeds 12 Pa [not (dP$_h$)], then processing unit 406 determines the fall solely based on the accelerometer data. For instance, determining the fall based on the accelerometer data is explained in WO2010055450A1. Any other algorithm to determine fall based on the accelerometer may as well be used.

Figure 5:
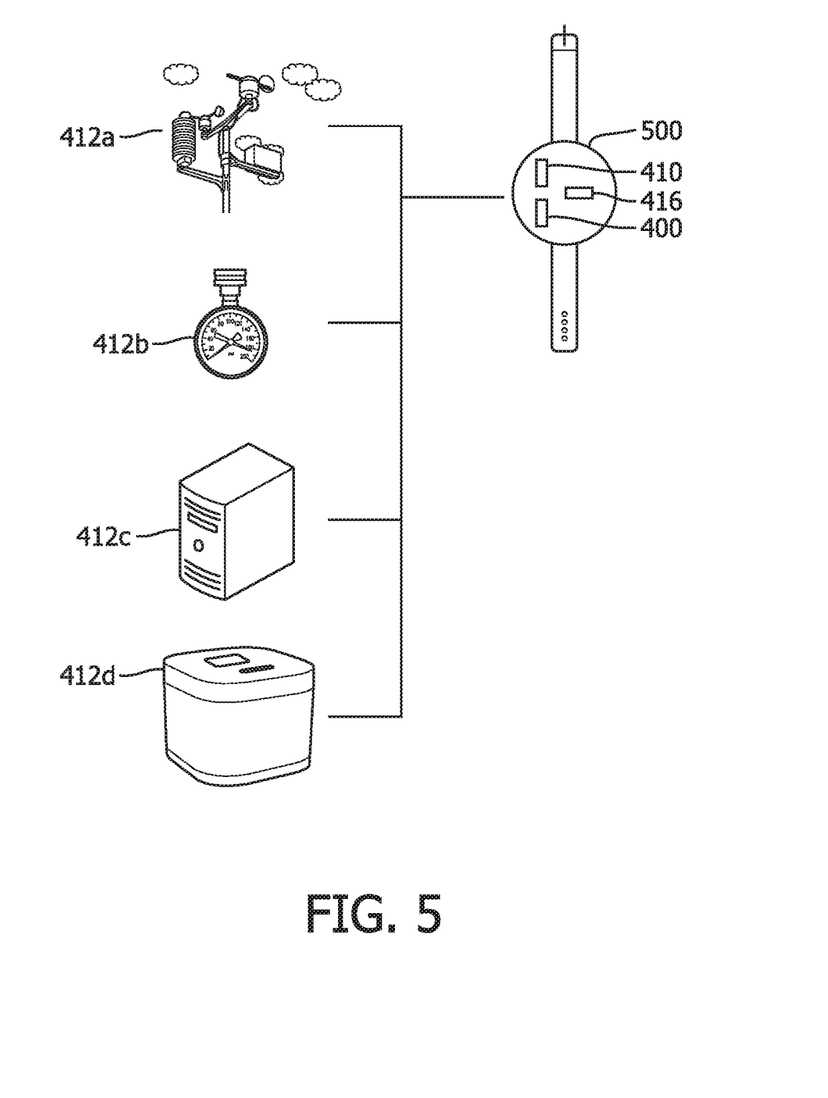
FIG. 5 shows a wearable device including the device according to an embodiment.

FIG. 5 shows a wearable device 500 including the device according to an embodiment. In the current embodiment, the device 400 as explained before is included in the wearable device 500, also may be referred to as a device 500 worn by the user. The device 500 includes the air-pressure sensor 410 and optionally may include the accelerometer 416. Though, the device 500 is shown as a wrist worn device, it may be appreciated that the device 408 may be as well a neck worn device, a chest worn device, etc.

In the current embodiment, the device 500 directly interacts with at least one wind speed sensor 412a, the air-pressure sensor 412b placed at a fixed height on a wall of the internal space where the user is located or integrated in a communicator/base unit 412d, and the weather station 412c. The fall is accordingly determined by the device 400, as also explained in FIG. 4, included in the wearable device 500.

Similar reference numerals for the modules/units/sensors indicate these modules/units/sensor perform in a similar manner and have similar technical capabilities.

In various embodiments, the term the processing unit 406, as used herein, may be any type of controller or processor, and may be embodied as one or more controllers or processors adapted to perform the functionality discussed herein. Additionally, as the term processor is used herein, a processor may include use of a single integrated circuit (IC), or may include use of a plurality of integrated circuits or other components connected, arranged or grouped together, such as controllers, microprocessors, digital signal processors, parallel processors, multiple core processors, custom ICs, application specific integrated circuits, field programmable gate arrays, adaptive computing ICs, associated memory, such as and without limitation, RAM, DRAM and ROM, and other ICs and components.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. Furthermore, any patent document or a publication mentioned herein is hereby incorporated by reference.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A computer implemented method for detecting a fall of a user within an internal space of a building, the method comprising:
   receiving a first air-pressure sensor signal indicative of change in air-pressure measured at a device worn by the user;
   receiving a measurement indicative of change in air-pressure within the internal space of the building, wherein the measurement is derived by synchronizing and averaging multiple measurements of change in pressure of devices worn by a plurality of users in a plurality of buildings in a neighborhood of the building; and
   determining the fall of the user based on the change in air-pressure measured at the device and the measurement indicative of change in the air-pressure within the internal space of the building.

2. The computer implemented method according to claim 1, further comprising:
   receiving the measurement indicative of change in the air-pressure within the internal space of the building from an air-pressure sensor placed at a fixed height within the internal space of the building.

3. The computer implemented method according to claim 1, further comprising:
   calculating the measurement indicative of change in the air-pressure within the internal space of the building based on a wind speed outside the building.

4. The computer implemented method according to claim 1, further comprising:
   deriving the measurement indicative of change in the air-pressure within the internal space of the building based on a statistical measure of the air-pressure measured in a plurality of buildings in a neighborhood of the building.

5. The computer implemented method according to claim 1, wherein the determining the fall of the user further comprises:
   determining an air-pressure value based on the change in air-pressure measured at the device and the measurement indicative of change in the air-pressure within the internal space of the building;
   comparing the air-pressure value with a pre-determined air-pressure threshold; and
   determining the fall based on the comparison.

6. A non-transitory computer-readable medium comprising instructions that are configured, when run on a computer, to receive signals from an air pressure sensor integrated in a device worn by a user and to detect a fall of a user within an internal space of a building, the non-transitory computer-readable medium comprising:
   instructions for receiving a first air-pressure sensor signal indicative of change in air-pressure measured at a device worn by the user;
   instructions for receiving a measurement indicative of change in air-pressure within the internal space of the building, wherein the measurement is derived by synchronizing and averaging multiple measurements of change in pressure of devices worn by a plurality of users in a plurality of buildings in a neighborhood of the building; and
   instructions for determining the fall of the user based on the change in air-pressure measured at the device and the measurement indicative of change in the air-pressure within the internal space of the building.

7. An apparatus configured for detecting a fall of a user within an internal space of a building, the apparatus comprising:
   an air-pressure interface configured to receive a first air-pressure signal indicative of change in air-pressure measured at a device worn by the user;
   a building air pressure interface to receive a measurement indicative of change in air-pressure within the internal space of the building, wherein the measurement is derived by synchronizing and averaging multiple measurements of change in pressure of devices worn by a plurality of users in a plurality of buildings in a neighborhood of the building; and
   a processing unit configured to determine the fall of the user based on the change in air-pressure measured at the device and the measurement indicative of change in the air-pressure within the internal space of the building.

8. The apparatus according to claim 7, wherein the building air pressure interface is configured to receive the measurement indicative of change in the air-pressure within the internal space of the building from an air-pressure sensor placed at a fixed height within the internal space of the building.

9. The apparatus according to claim 7, wherein the building air pressure interface is configured to receive the measurement indicative of change in the air-pressure within the internal space of the building from the processing unit, and the processing unit is configured to calculate the measurement indicative of the change in air-pressure within the internal space of the building based on a wind speed outside of the building.

10. The apparatus according to claim 9, wherein the wind speed is received from at least one of a wind sensor module placed outside of the building and a weather station.

11. The apparatus according to claim 10, wherein the wind speed is a real-time wind speed.

12. The apparatus according to claim 7, wherein the building air pressure interface is configured to receive the measurement indicative of change in the air-pressure within the internal space of the building from the processing unit, and the processing unit is configured to calculate the measurement of the air-pressure within the internal space of the building based on a statistical measure of the air-pressure measured in the plurality of buildings in the neighborhood of the building.

13. The apparatus according to claim 7, wherein the processing unit is configured to determine the fall by:
   determining an air-pressure value based on the change in air-pressure measured at the device and the measurement indicative of change in the air-pressure within the internal space of the building;
   comparing the air-pressure value with a pre-determined air-pressure threshold; and
   determining the fall based on the comparison.

14. A device configured to be worn by the user comprising:
   an air pressure sensor configured to measure the air-pressure at the device worn by the user; and
   the apparatus according to claim 7.

15. A system configured for detecting the fall of the user, the system comprising:
   the device according to claim 14; and
   at least one of a wind sensor module and a weather station configured to provide a wind speed outside of the building of the user.

* * * * *